(12) United States Patent
Lehmann et al.

(10) Patent No.: US 7,046,362 B2
(45) Date of Patent: *May 16, 2006

(54) FIBER-OPTIC BASED CAVITY RING-DOWN SPECTROSCOPY APPARATUS

(75) Inventors: Kevin K. Lehmann, Lawrence, NJ (US); Peter B. Tarsa, Duxbury, MA (US); Paul Rabinowitz, Bridgewater, NJ (US)

(73) Assignee: Trustees of Princeton University, Princeton, NJ (US)

( * ) Notice: Subject to any disclaimer, the term of this patent is extended or adjusted under 35 U.S.C. 154(b) by 88 days.

This patent is subject to a terminal disclaimer.

(21) Appl. No.: 10/017,367

(22) Filed: Dec. 12, 2001

(65) Prior Publication Data

US 2003/0107739 A1    Jun. 12, 2003

(51) Int. Cl.
*G01N 21/00* (2006.01)

(52) U.S. Cl. .................. 356/437; 250/227.14; 436/164

(58) Field of Classification Search ................ 356/300, 356/432–437, 440; 250/343, 227, 14; 385/12, 385/15; 359/834, 836; 355/432–440; 436/164
See application file for complete search history.

(56) References Cited

U.S. PATENT DOCUMENTS

| | | | |
|---|---|---|---|
| 1,719,443 A | 7/1929 | Nichterlein | |
| 3,402,364 A | 9/1968 | De Lang | |
| 3,711,788 A | 1/1973 | Forkner | |
| 3,976,368 A | 8/1976 | McCann et al. | |
| 3,982,203 A | 9/1976 | De Wit | |
| 4,161,436 A | 7/1979 | Gould | |
| 4,525,034 A | 6/1985 | Simmons | |
| 4,530,603 A * | 7/1985 | Shaw et al. ................. | 356/480 |
| 4,677,639 A | 6/1987 | Sasser | |
| 4,740,986 A | 4/1988 | Reeder | |
| 4,746,201 A | 5/1988 | Gould | |
| 4,775,214 A * | 10/1988 | Johnson ....................... | 385/12 |
| 5,026,991 A | 6/1991 | Goldstein et al. | |
| 5,168,156 A * | 12/1992 | Fischer et al. ......... | 250/227.21 |
| 5,276,548 A | 1/1994 | Margalith | |
| 5,463,493 A | 10/1995 | Shah | |
| 5,483,342 A | 1/1996 | Rockwell | |
| 5,528,040 A | 6/1996 | Lehmann | |
| 5,835,231 A | 11/1998 | Pipino | |
| 5,912,740 A | 6/1999 | Zare et al. | |
| 5,973,864 A | 10/1999 | Lehmann et al. | |
| 5,986,768 A * | 11/1999 | Pipino ........................ | 356/440 |

(Continued)

FOREIGN PATENT DOCUMENTS

DE    19814575 A1    10/1999

(Continued)

OTHER PUBLICATIONS

U.S. Appl. No. 60/331,181.*

(Continued)

*Primary Examiner*—Hoa Q. Pham
(74) *Attorney, Agent, or Firm*—RatnerPrestia (57) ABSTRACT

An apparatus for detection and measurement of trace species in a gas or liquid sample. A ring down cell formed from a fiber optic ring is exposed to the sample gas or liquid. A coherent source emits radiation into the fiber optic ring, which in turn is received at an output thereof. The fiber optic ring has a portion thereof, between the input and output, exposed to the sample gas or sample liquid. A processor is coupled to the receiver and determines the level of trace species in the gas or liquid sample based on the rate of decay of the radiation within the fiber optic ring.

56 Claims, 11 Drawing Sheets

U.S. PATENT DOCUMENTS

| | | | |
|---|---|---|---|
| 6,097,555 | A | 8/2000 | Lehmann et al. |
| 6,172,823 | B1 | 1/2001 | Lehmann et al. |
| 6,172,824 | B1* | 1/2001 | Lehmann et al. ............ 359/834 |
| 6,466,322 | B1* | 10/2002 | Paldus et al. ................ 356/437 |
| 6,532,072 | B1* | 3/2003 | Largent ....................... 356/440 |
| 2002/0092977 | A1* | 7/2002 | Lerber et al. ........... 250/227.14 |
| 2003/0007715 | A1* | 1/2003 | Loock et al. .................. 385/12 |
| 2003/0109055 | A1* | 6/2003 | Lehmann et al. ............ 436/164 |

FOREIGN PATENT DOCUMENTS

| | | |
|---|---|---|
| JP | 63013386 | 1/1988 |

OTHER PUBLICATIONS

U.S. Appl. No. 60/293,518.*

Stewart G., et al., "Intra-cavity and ring-down cavity absorption with fibre amplifiers for trace gas detection" SPIE 4185, 448-451 (2000).*

Atherton, K. et al., "fibre optic intra-cavity spectroscopy-combined ring down and ICLAS architectures using fibre lasers" SPIE 4204: 124-130 (2001).*

J. White, Long Optical Paths of Large Aperture, 32 *J. Opt. Soc. Amer.*, 285 (May, 1942).

D. Heriott et al., Off-Axis Paths in Spherical Mirror Interferometers, 3 *Appl. Opt.* (4), 523 (Apr., 1964).

A. O'Keefe & D. Deacon, Cavity Ring-Down Optical Spectrometer for Absorption Measurements Using Pulsed Laser Sources, 59 *Rev. Sci. Instrum.*, 2544 (Dec., 1988).

D. Romanini & K. Lehmann, Ring-Down Cavity Absorptionn Spectroscopy of the Very Weak HCN Overtone Bands With Six, Seven, and Eight Stretching Quanta, 99 *J. Chem. Phys.* (9), 6287 (Nov. 1, 1993).

G. Rempe et al., Measurement of Ultralow Losses in an Optical Interferometer, 17 *Opt. Letters* (5), 363 (Mar. 1, 1992).

T. Yu & M. Lin, Kinetics of Phenyl Radical Reactions Studied by the "Cavity-Ring-Down" Method, 115 *J. Am. Chem. Soc.*, 4371 (1993).

G. Meijer et al., Coherent Cavity Ring Down Spectroscopy, 217 *Chemical Physics Letters* (1,2), 112 (Jan. 7, 1994).

J. Scherer et al., Cavity Ring Down Dye Laser Spectroscopy of Jet-Cooled Metal Clusters: $CU_2$ and $CU_3$, 172 *Chemical Physics Letters* (3,4), 214 (Sep. 7, 1990).

F. Stoelkel & G. Atkinson, Time Evolution of Broadband Quasi-cw Dye Laser: Limitation of Sensitivity in Intracavity Laser Spectroscopy, 24 *Applied Optics* (21), 3591 (Nov. 1, 1985).

K. Lehmann & D. Romanini, Molecules in the Stellar Environment, *Experimental Measurement of Weak Band Intensities in Molecules in the Stellar Environment*, (Springer, 1994).

G. Gould et al., Crossed Roof Prism Interferometer, 1 *Applied Optics* (4), 533 (Jul. 1962).

A. Pipino et al., Evanescent Wave Cavity Ring-Down Spectroscopy with a Total-Internal Reflection Minicavity, 68 (8) *Rev. Sci, Instrum.*, 2978 (Aug. 1997).

Stewart G, Atherton K, Yu H, Culsbaw B. "An investigation of an optical fibre amplifier loop for intra-cavity and ring-down cacity loss measurements." *Meas. Sci. Technol.* 12: 843-849 (2001).

Dmitriev Al, Yanshen Z, Xinyu M. "Optical-fiber passive ring resonator in a low-mode radiation-propogration regime." *J. Opt. Technol.* 67: 219-221 (2000).

Blair S, Chen Y. "Resonant-enhanced evanescent-wave fluorescence biosensing with cylindrical optical cavities," *Applied Optics*, 40: 570-582 (2001).

Littlejohn D, Lucas D, Han L. "Bent Silica Fiber Evanescent Absorption Sensors for Near-Infrared Spectroscopy." *Applied Spectroscopy.* 53: 845-849 (1999).

Messica A, Greenstein A, Katzir A. "Theory of fiber-optic evanescent-wave spectroscopy and sensors." *Applied Optics* 35: 2274-2284 (1996).

Trautmann et al., "Determination of the Deuterium Abundance in Water Using a CW Chemical DF Laser", *Appl. Phys.*, 24: No. 1, 49-53 (1981).

Spammer, S, Swart, P, Booysen, A. "Interferometric distributed optical-fiber sensor", *Applied Optics* vol. 35, No. 22: 4522-4525 (Aug. 1996).

International Search Report dated May 16, 2003, application No. PCT/US 02/38421.

* cited by examiner

FIG. 1

Prior Art

Prior Art

FIBER-OPTIC BASED CAVITY RING-DOWN SPECTROSCOPY APPARATUS

FIELD OF THE INVENTION

This invention relates generally to absorption spectroscopy and, in particular, is directed to the use of a fiber-optic resonator for ring-down cavity spectroscopy.

BACKGROUND OF THE INVENTION

Figure 1:
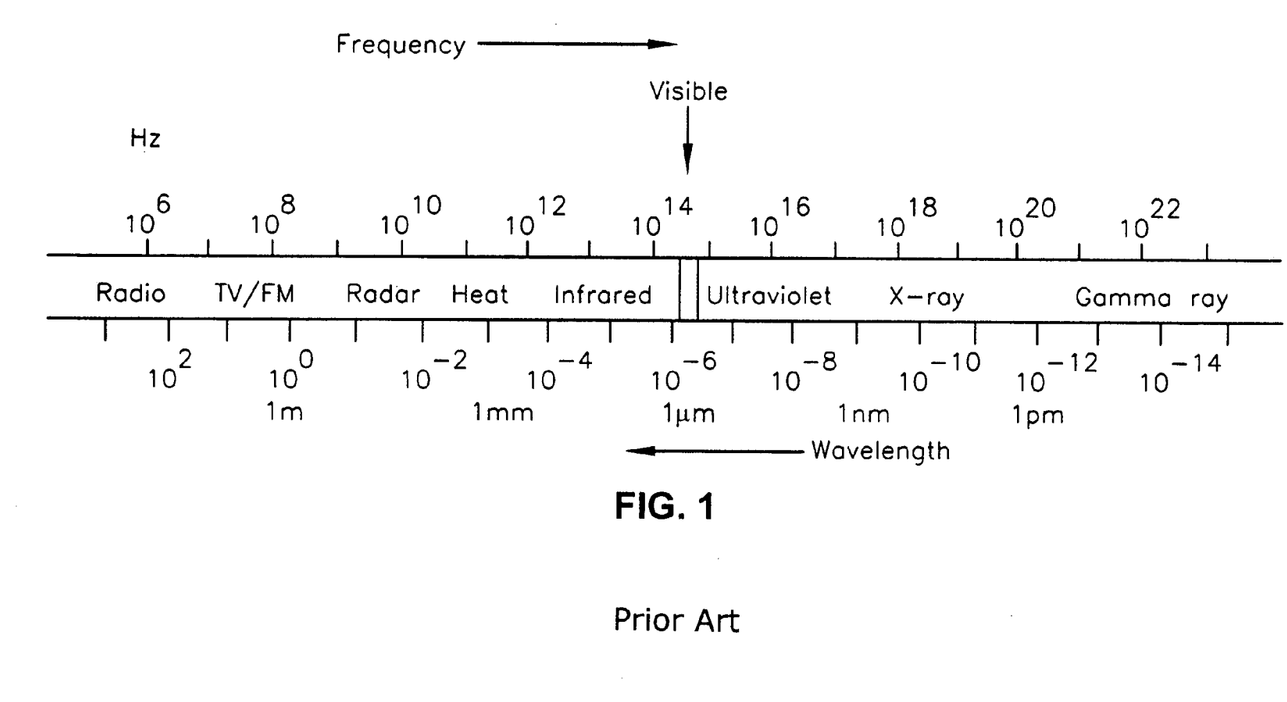
FIG. 1 illustrates the electromagnetic spectrum on a logarithmic scale.

Referring now to the drawing, wherein like reference numerals refer to like elements throughout, FIG. 1 illustrates the electromagnetic spectrum on a logarithmic scale. The science of spectroscopy studies spectra. In contrast with sciences concerned with other parts of the spectrum, optics particularly involves visible and near-visible light—a very narrow part of the available spectrum which extends in wavelength from about 1 mm to about 1 nm. Near visible light includes colors redder than red (infrared) and colors more violet than violet (ultraviolet). The range extends just far enough to either side of visibility that the light can still be handled by most lenses and mirrors made of the usual materials. The wavelength dependence of optical properties of materials must often be considered.

Absorption-type spectroscopy offers high sensitivity, response times on the order of microseconds, immunity from poisoning, and limited interference from molecular species other than the species under study. Various molecular species can be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp spectral lines. The narrow lines in the spectrum can be used to discriminate against most interfering species.

In many industrial processes, the concentration of trace species in flowing gas streams and liquids must be measured and analyzed with a high degree of speed and accuracy. Such measurement and analysis is required because the concentration of contaminants is often critical to the quality of the end product. Gases such as $N_2$, $O_2$, $H_2$, Ar, and He are used to manufacture integrated circuits, for example, and the presence in those gases of impurities—even at parts per billion (ppb) levels—is damaging and reduces the yield of operational circuits. Therefore, the relatively high sensitivity with which water can be spectroscopically monitored is important to manufacturers of high-purity gases used in the semiconductor industry. Various impurities must be detected in other industrial applications. Further, the presence of impurities, either inherent or deliberately place, in liquids have become of particular concern of late.

Spectroscopy has obtained parts per million (ppm) level detection for gaseous contaminants in high-purity gases. Detection sensitivities at the ppb level are attainable in some cases. Accordingly, several spectroscopic methods have been applied to such applications as quantitative contamination monitoring in gases, including: absorption measurements in traditional long pathlength cells, photoacoustic spectroscopy, frequency modulation spectroscopy, and intracavity laser absorption spectroscopy. These methods have several features, discussed in U.S. Pat. No. 5,528,040 issued to Lehmann, which make them difficult to use and impractical for industrial applications. They have been largely confined, therefore, to laboratory investigations.

In contrast, cavity ring-down spectroscopy (CRDS) has become an important spectroscopic technique with applications to science, industrial process control, and atmospheric trace gas detection. CRDS has been demonstrated as a technique for the measurement of optical absorption that excels in the low-absorbance regime where conventional methods have inadequate sensitivity. CRDS utilizes the mean lifetime of photons in a high-finesse optical resonator as the absorption-sensitive observable.

Typically, the resonator is formed from a pair of nominally equivalent, narrow band, ultra-high reflectivity dielectric mirrors, configured appropriately to form a stable optical resonator. A laser pulse is injected into the resonator through a mirror to experience a mean lifetime which depends upon the photon round-trip transit time, the length of the resonator, the absorption cross section and number density of the species, and a factor accounting for intrinsic resonator losses (which arise largely from the frequency-dependent mirror reflectivities when diffraction losses are negligible). The determination of optical absorption is transformed, therefore, from the conventional power-ratio measurement to a measurement of decay time. The ultimate sensitivity of CRDS is determined by the magnitude of the intrinsic resonator losses, which can be minimized with techniques such as superpolishing that permit the fabrication of ultra-low-loss optics.

At present, CRDS is limited to spectroscopic regions where high reflectivity dielectric mirrors can be used. This has significantly limited the usefulness of the method in much of the ultraviolet and infrared regions, because mirrors with sufficiently high reflectivity are not presently available. Even in regions where suitable dielectric mirrors are available, each set of mirrors only allows for operation over a small range of wavelengths, typically a fractional range of a few percent. Further, construction of many dielectric mirrors requires use of materials that may degrade over time, especially when exposed to chemically corrosive environments. Because these present limitations restrict or prevent the use of CRDS in many potential applications, there is a clearly recognized need to improve upon the current state of the art with respect to resonator construction.

The article by A. Pipino et al., "Evanescent wave cavity ring-down spectroscopy with a total-internal reflection mini-cavity," Rev. Sci. Instrum. 68 (8) (August 1997), presents one approach to an improved resonator construction. The approach uses a monolithic, total internal reflection (TIR) ring resonator of regular polygonal geometry (e.g., square and octagonal) with at least one convex facet to induce stability. A light pulse is totally reflected by a first prism located outside and in the vicinity of the resonator, creating an evanescent wave which enters the resonator and excites the stable modes of the resonator through photon tunneling. When light impinges on a surface of lower index of refraction that the propagation medium at greater than a critical angle, it reflects completely. J. D. Jackson, "Classical Electrodynamics," Chapter 7, John Wiley & Sons, Inc.: New York, N.Y. (1962). A field exists, however, beyond the point of reflection that is non-propagating and decays exponentially with distance form the interface. This evanescent field carries no power in a pure dielectric medium, but attenuation of the reflected wave allows observation of the presence of an absorbing species in the region of the evanescent field. F. M. Mirabella (ed.), "Internal Reflection Spectroscopy," Chapter 2, Marcel Dekker, Inc.: New York, N.Y. (1993).

The absorption spectrum of matter located at the totally reflecting surfaces of the resonator is obtained from the mean lifetime of a photon in the monolithic resonator, which is extracted from the time dependence of the signal received at a detector by out coupling with a second prism (also a totally reflecting prism located outside, but in the vicinity of, the resonator). Thus, optical radiation enters and exits the resonator by photon tunneling, which permits precise control of input and output coupling. A miniature-resonator realization of CRDS results and the TIR-ring resonator extends the CRDS concept to condensed matter spectroscopy. The broadband nature of TIR circumvents the narrow bandwidth restriction imposed by dielectric mirrors in conventional gas-phase CRDS. The work of A. Pipino et al. is only applicable to TIR spectroscopy, which is intrinsically limited to short overall absorption pathlengths, and thus powerful absorption strengths. In contrast, the present invention provides long absorption pathlengths and thus allows for detection of weak absorption strengths.

Various novel approaches to mirror based CRDS systems are provided in U.S. Pat. Nos. 5,973,864, 6,097,555, 6,172,823 B1, and 6,172,824 B1 issued to Lehmann et al., and incorporated herein by reference. These approaches teach the use of a near-confocal resonator formed by two reflecting elements or prismatic elements.

Figure 2:
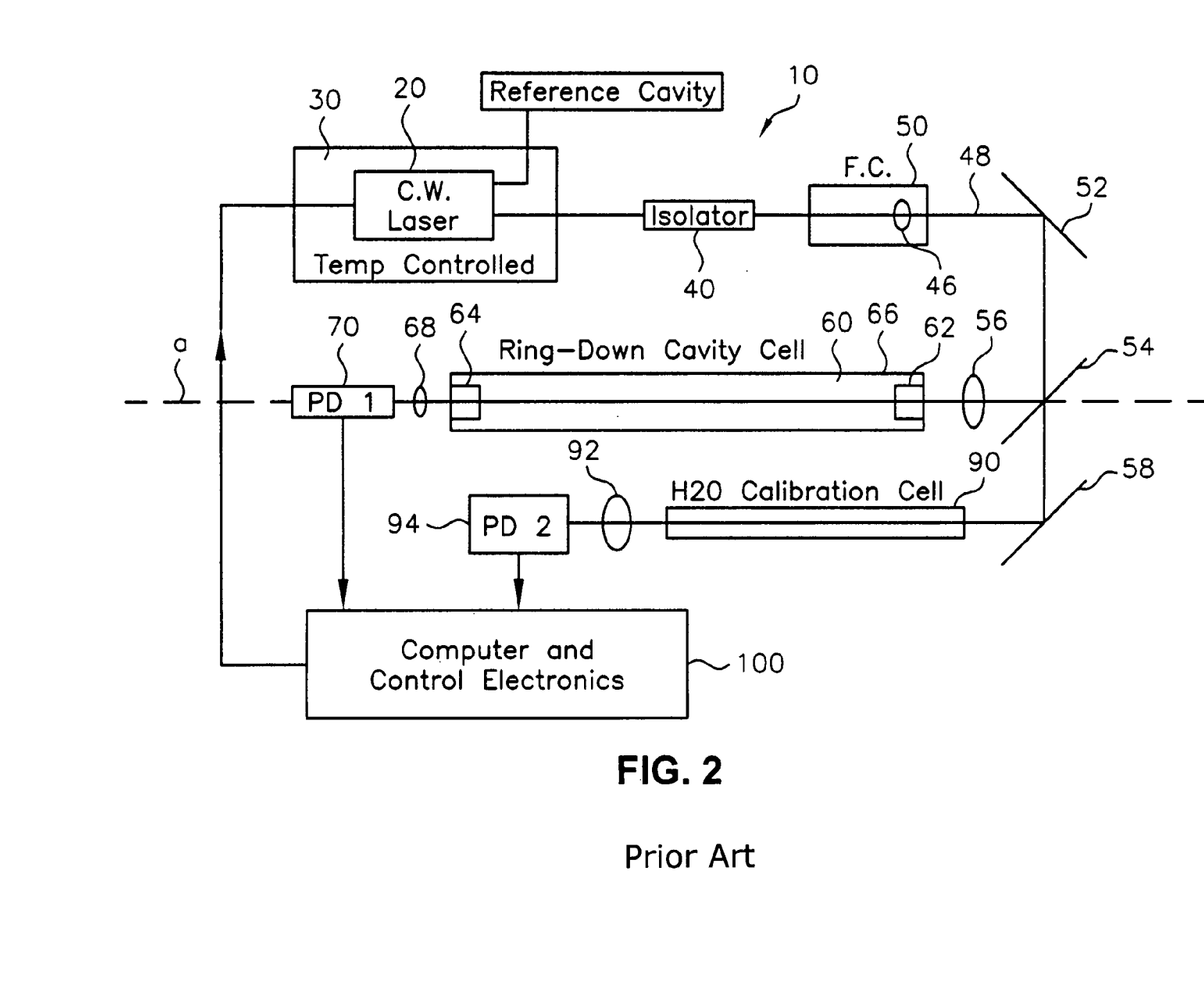
FIG. 2 illustrates a prior art CRDS system using mirrors.

FIG. 2 illustrates a prior art CRDS apparatus 10. As shown in FIG. 2, light is generated from a narrow band, tunable, continuous wave diode laser 20. Laser 20 is temperature tuned by a temperature controller 30 to put its wavelength on the desired spectral line of the analyte. An isolator 40 is positioned in front of and in line with the radiation emitted from laser 20. Isolator 40 provides a one-way transmission path, allowing radiation to travel away from laser 20 but preventing radiation from traveling in the opposite direction. Single mode fiber coupler (F.C.) 50 couples the light emitted from laser 20 into the optical fiber 48. Fiber coupler 50 is positioned in front of and in line with isolator 40. Fiber coupler 50 receives and holds optical fiber 48 and directs the radiation emitted from laser 20 toward and through a first lens 46. First lens 46 collects and focuses the radiation. Because the beam pattern emitted by laser 20 does not perfectly match the pattern of light propagating in optical fiber 48, there is an inevitable mismatch loss.

The laser radiation is approximately mode-matched into a ring down cavity (RDC) cell 60. A reflective mirror 52 directs the radiation toward a beam splitter 54. Beam splitter 54 directs about 90%, of the radiation through a second lens 56. Second lens 56 collects and focuses the radiation into cell 60. The remaining radiation passes through beam splitter 54 and is directed by a reflective mirror 58 into an analyte reference cell 90.

The radiation which is transmitted through analyte reference cell 90 is directed toward and through a fourth lens 92. Fourth lens 92 is aligned between analyte reference cell 90 and a second photodetector 94 (PD 2). Photodetector 94 provides input to computer and control electronics 100.

Cell 60 is made from two, highly reflective mirrors 62, 64, which are aligned as a near confocal etalon along an axis, a. Mirrors 62, 64 constitute the input and output windows of cell 60. The sample gas under study flows through a narrow tube 66 that is coaxial with the optical axis, a, of cell 60. Mirrors 62, 64 are placed on adjustable flanges or mounts that are sealed with vacuum tight bellows to allow adjustment of the optical alignment of cell 60.

Mirrors 62, 64 have a high-reflectivity dielectric coating and are oriented with the coating facing inside the cavity formed by cell 60. A small fraction of laser light enters cell 60 through front mirror 62 and "rings" back and forth inside the cavity of cell 60. Light transmitted through rear mirror 64 (the reflector) of cell 60 is directed toward and through a third lens 68 and, in turn, imaged onto a first photodetector 70 (PD 1). Each of photodetectors 70, 94 converts an incoming optical beam into an electrical current and, therefore, provides an input signal to computer and control electronics 100. The input signal represents the decay rate of the cavity ring down.

Figure 3:
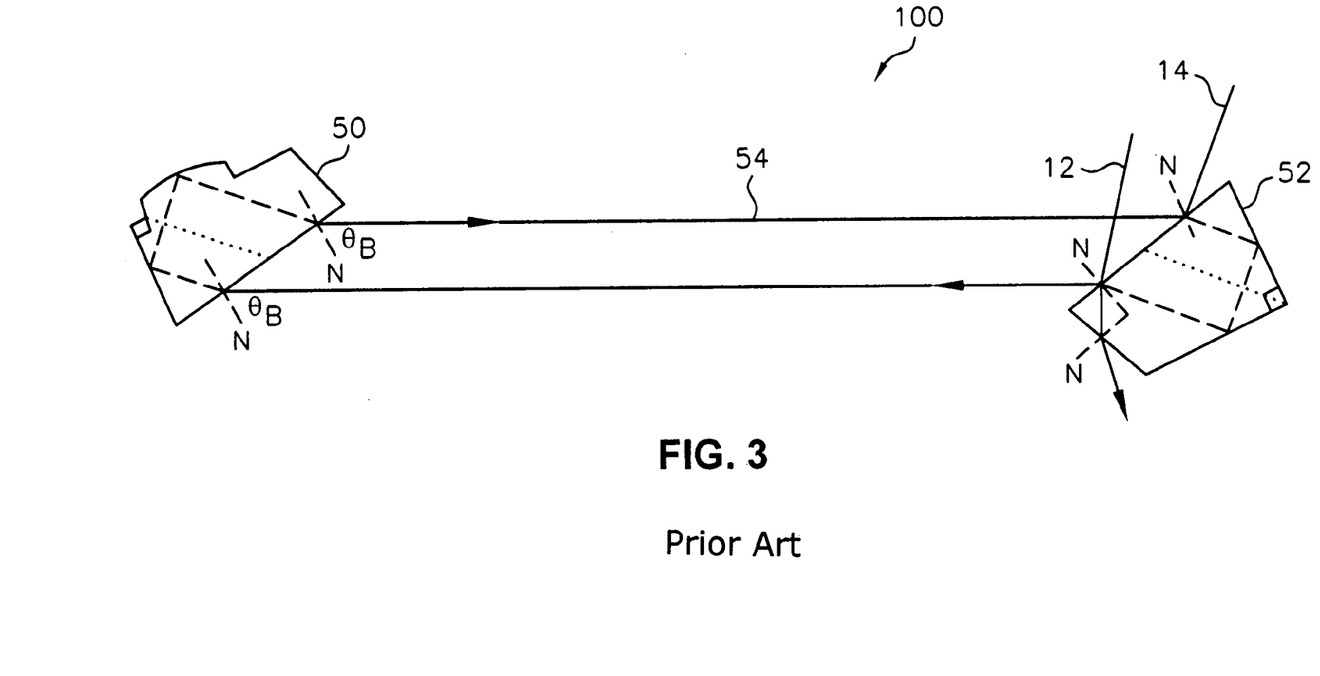
FIG. 3 illustrates a prior art CRDS cell using prisms.

FIG. 3 illustrates optical path within a prior art CRDS resonator 100. As shown in FIG. 3, resonator 100 for CRDS is based upon using two Brewster's angle retroreflector prisms 50, 52. The polarizing or Brewster's angle, $\Theta_B$, is shown relative to prism 50. Incident light 12 and exiting light 14 are illustrated as input to and output from prism 52, respectively. The resonant optical beam undergoes two total internal reflections without loss in each prism 50, 52 at about 45°, an angle which is greater than the critical angle for fused quartz and most other common optical prism materials. Light travels between prisms 50, 52 along optical axis 54.

Although, when compared with the other spectroscopy methods, ring down cavity spectroscopy is a simpler and less expensive to implement, it is still costly in that a ring down cavity spectroscopy system can cost on the order of many thousands of dollars per unit. In addition, conventional CRDS devices are prone to misalignment between the optical elements while being fabricated as well as during use.

To overcome the shortcomings of the known approaches to improved resonator construction, a new optic-fiber based optical resonator for CRDS is provided. An object of the present invention is to replace the conventional dielectric mirrors or prism retroreflectors, thereby providing a more durable and lower cost resonator.

SUMMARY OF THE INVENTION

To achieve that and other objects, and in view of its purposes, the present invention provides an improved apparatus for trace species detection and measurement in a sample gas. The apparatus includes a passive fiber optic cable having a portion thereof exposed to the sample gas or sample liquid; a coherent source of radiation; a coupler for i) introducing a portion of the radiation emitted by the coherent source to the passive fiber optic ring and ii) receiving a portion of the radiation introduced into the passive fiber optic ring; a detector for detecting a level of the radiation received by the coupling means and generating a signal responsive thereto; and a processor coupled to the detector for determining a level of the trace species in the gas sample or liquid sample based on the signal generated by the detector.

According to another aspect of the invention, the level of the trace species is determined based on a rate of decay of the signal generated by the detector means.

According to a further aspect of the invention, a filter is placed between the coupling means and the detector to selectively pass the received portion of radiation from the passive fiber optic loop to the detector.

According to yet another aspect of the invention, the coupler includes i) a first coupler for introducing the portion of the radiation emitted by the coherent source to a first section of the fiber optic ring and ii) a second coupler for receiving the portion of the radiation in the passive fiber optic ring at a second section thereof.

According to still another aspect of the invention, the exposed portion of the fiber is the cladding of the fiber.

According to yet a further aspect of the invention, the exposed portion of the fiber is the inner core of the fiber.

According to another aspect of the invention, the coherent source is an optical parametric generator, an optical parametric amplifier, or a laser.

According to yet another aspect of the invention, an evanescent field of the radiation traveling within the fiber is exposed to the sample gas or sample liquid.

According to still another aspect of the invention, the absorption of the radiation from the fiber increases a rate of decay of the radiation.

According to yet a further aspect of the invention, the passive resonant fiber has a hollow core.

According to yet another aspect of the invention, the apparatus further comprises a sensor formed from a cylindrical body and wrapped with a section of the exposed portion of the resonant fiber such that exposure of the evanescent field to the trace species is enhanced by increasing the penetration depth of the evanescent field.

According to a further aspect of the invention, at least a portion of the passive fiber optic ring is coated with a material to selectively increase a concentration of the trace species at the coated portion of the fiber optic ring.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 4:
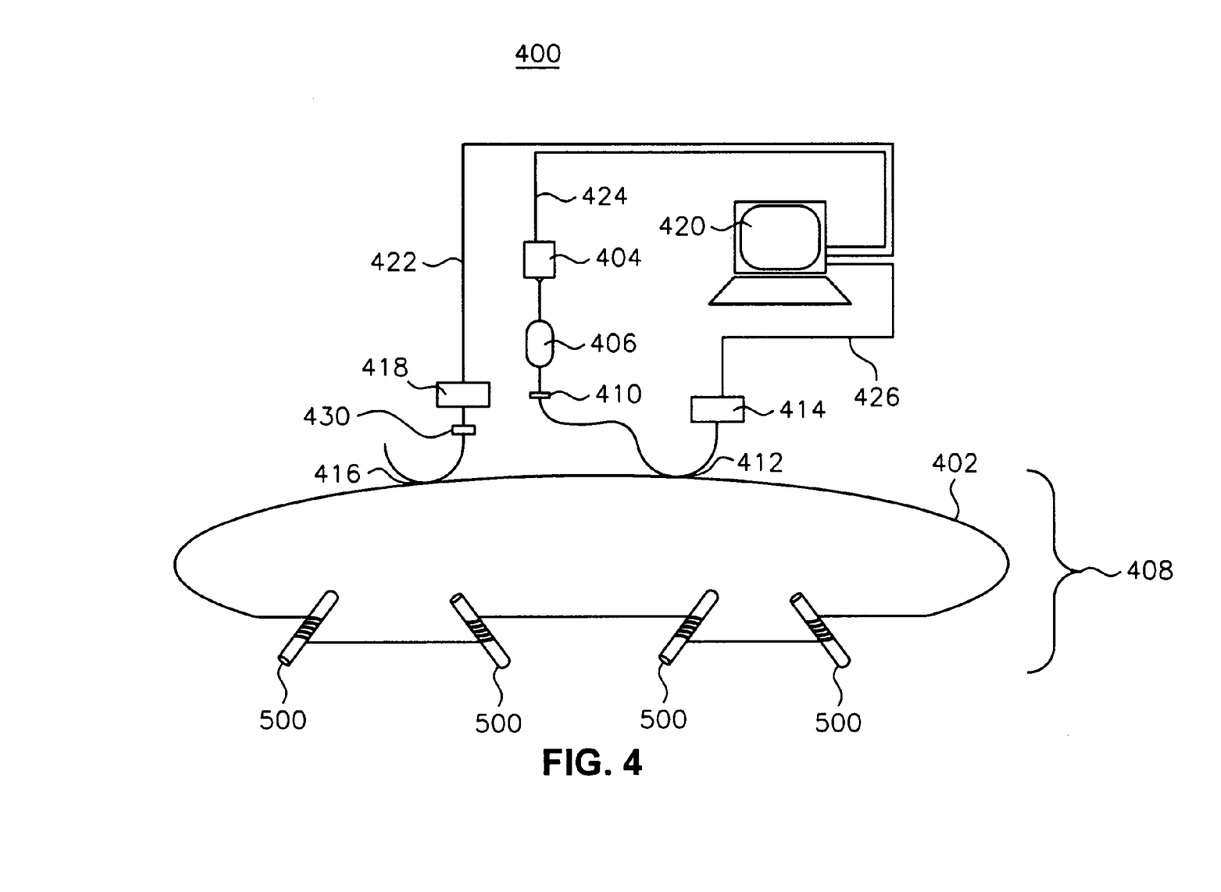
FIG. 4 is an illustration of a first exemplary embodiment of the present invention.

FIG. 4 illustrates fiber optic based ring-down apparatus 400 according to a first exemplary embodiment of the present invention through which trace species, or analytes, in gases and liquids may be detected. In FIG. 4, apparatus 400 includes resonant fiber optic ring 408 which has fiber optic cable 402 and sensors 500 (described below in detail) distributed along the length of fiber optic cable 402. The length of resonant fiber optic ring 408 is easily adaptable to a variety of acquisition situations, such as perimeter sensing or passing through various sections of a physical plant, for example. Although as shown, sensors 500 are distributed along the length of fiber optic loop 408, the invention may be practiced using only one sensor 500, if desired. The distribution of more than one sensor 500 allows for sampling of a trace species at various points throughout the installation site. The invention may also be practiced using a combination of sensors 500 with straight section of fiber 402 exposed to sample liquids or gases, or with only straight sections of fiber 402 exposed to the sample liquid or gas. It is contemplated that the length of resonant fiber optic ring may be as small as about 1 meter or as large as several kilometers.

Coherent source of radiation 404, such as an optical parametric generator (OPG), optical parametric amplifier (OPA) or a laser, for example, emits radiation at a wavelength consistent with an absorption frequency of the analyte or trace species of interest. Coherent source 404 may be a tunable diode laser having a narrow band based on the trace species of interest. An example of a commercially available optical parametric amplifier is model no. OPA-800C available from Spectra Physics, of Mountain View, Calif.

Examples of frequencies of coherent source 404 versus analytes are outlined in Table 1. Table 1 is merely illustrative and not intended as restrictive of the scope of the present invention. Further, it is contemplated that the present invention may be used to detect a variety of chemical and biological agents harmful to humans and/or animals. It is also contemplated that such detection may be enhanced by coating the surface of the passive fiber optic ring with antibodies that specifically bind the desired antigen.

TABLE 1

| Analyte or Trace Species | Approximate Wavelength(s) Near Infrared | Approximate Wavelength(s) Mid Infrared |
|---|---|---|
| Water ($H_2O$) | 1390 nm | 5940 nm |
| Ammonia ($NH_3$) | 1500 nm | 10300 nm |
| Methane ($CH_4$) | 1650 nm | 3260 nm |
| Carbon Dioxide ($CO_2$) | 1960 nm | 4230 nm |
| Carbon Monoxide (CO) | 1570 nm; 2330 nm | 4600 nm |
| Nitric Oxide (NO) | 1800 nm; 2650 nm | 5250 nm |
| Nitrogen Dioxide ($NO_2$) | 2680 nm | 6140 nm |
| Nitrous Oxide ($N_2O$) | 2260 nm | 4470 nm |
| Sulfur Dioxide ($SO_2$) |  | 7280 nm |
| Acetylene | 1520 nm | 7400 nm |
| Hydrogen Fluoride (HF) | 1310 nm |  |

TABLE 1-continued

| Analyte or Trace Species | Approximate Wavelength(s) Near Infrared | Approximate Wavelength(s) Mid Infrared |
|---|---|---|
| Hydrogen Chloride (HCl) | 1790 nm | 3400 nm |
| Hydrogen Bromide (HBr) | 1960 nm | 3820 nm |
| Hydrogen Iodide (HI) | 1540 nm | |
| Hydrogen Cyanide (HCN) | 1540 nm | 6910 nm |
| Hydrogen Sulfide (H2S) | 1570 nm | |
| Ozone (O3) | | 9500 nm |
| Formaldehyde (H2CO) | 1930 nm | 3550 nm |
| Phosphine (PH3) | 2150 nm | 10100 nm |
| Oxygen (O2) | 760 nm | |

In the first exemplary embodiment, radiation from coherent source 404 is provided to resonant fiber optic ring 408 through optional optical isolator 406, coupler 410, and evanescent input coupler 412. When coherent source 404 is a diode laser, using optical isolator 406 provides the benefit of minimizing noise in the laser by preventing reflections back into the laser. Evanescent input coupler 412 may provide a fixed percentage of radiation from coherent source 404 into resonant fiber optic ring 408, or may be adjustable based on losses present throughout resonant fiber optic ring 408. Preferably, the amount of radiation provided by evanescent input coupler 412 to resonant fiber optic ring 408 matches the losses present in fiber optic cable 402 and the connectors (not shown). A commercially available evanescent coupler providing 1% coupling (99%/1% split ratio coupling) of radiation is manufactured by ThorLabs of Newton, N.J., having part number 10202A-99. In a preferred embodiment, evanescent input coupler 412 couples less that 1% of the radiation from coherent source 404 into fiber 402.

Figure 5A:
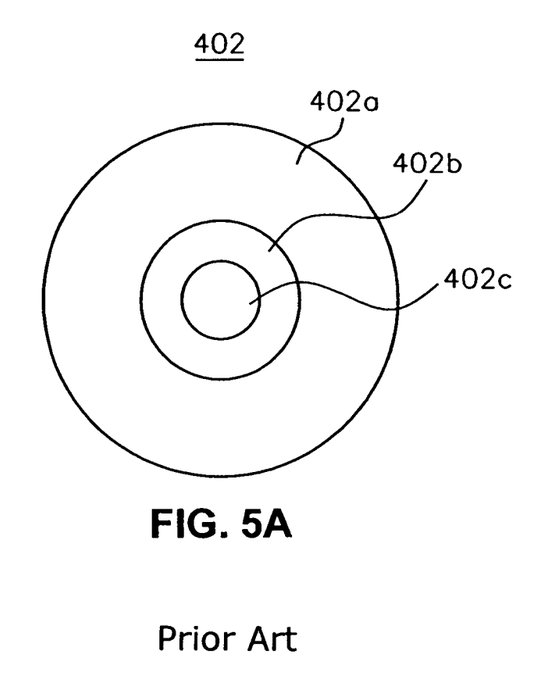
FIG. 5A is a end view of a conventional optical fiber.

In one exemplary embodiment, to detect the trace species or analyte, a portion of the jacket 402a covering the fiber optic cable 402 is removed to expose cladding 402b that surrounds inner core 402c of fiber optic cable 402. Alternatively, either both jacket 402a and cladding 402b may be removed to expose inner core 402c, or the jacketed portion of fiber optic cable 402 may be exposed to the sample liquid or gas. The latter approach may be useful for example, in the case where the evanescent field (discussed below) extends into the jacket for interaction with the trace species (which has been absorbed or dissolved into the jacket). Removing both the jacket and cladding may not be the most preferred, however, because of the brittle nature of inner core 402c used in certain types of fiber optic cables. A cross section of a typical fiber optic cable is shown in FIG. 5A.

Bending a total internal reflection (TIR) element changes the angle at which the incident electro-magnetic wave contacts the reflection surface. In the case of bending an optical fiber about a cylindrical body, the angle of reflection on the surface of the fiber core opposite the body is closer to normal, and the penetration depth of the evanescent field is increased. By wrapping several turns of optical fiber 402 around cylindrical core element 502 (see FIG. 5B), the evanescent field penetration depth is increased and a greater length of fiber can be exposed to the detection fluid in a smaller physical volume. An experimental, verification of the improvement in optical fiber sensing through varying bending radii is discussed by D. Littlejohn et al. in "Bent Silica Fiber Evanescent Absorption Sensors for Near Infrared Spectroscopy," Applied Spectroscopy 53: 845–849 (1999).

Figure 5B:
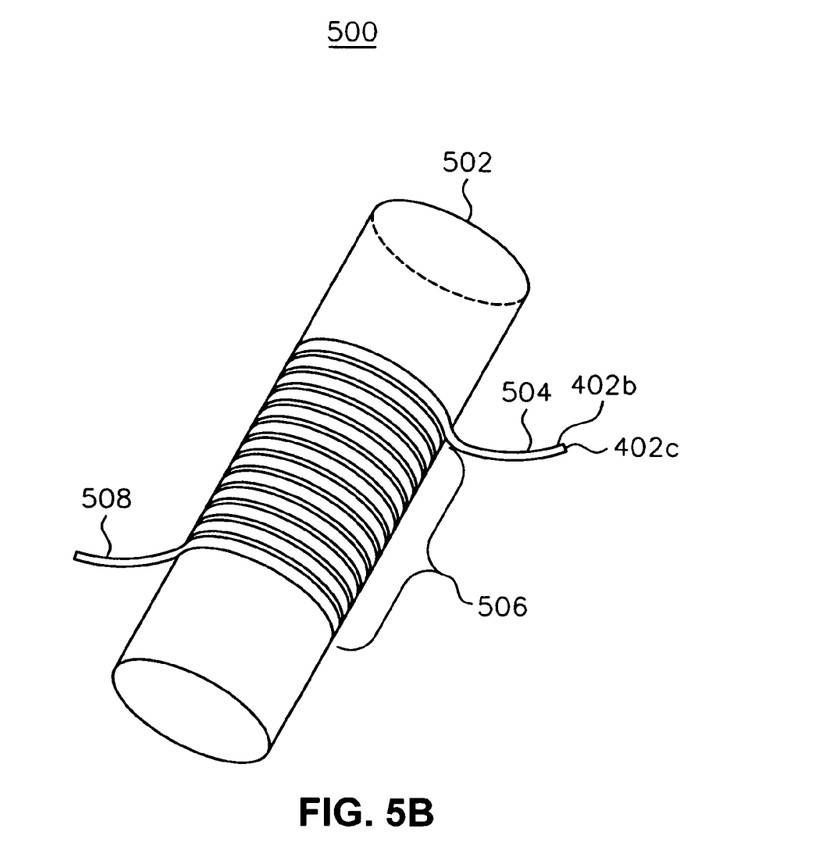
FIG. 5B is a perspective view of a sensor according to an exemplary embodiment of the present invention.

FIG. 5B illustrates an exemplary sensor 500 used to detect trace species in a liquid or gas sample. As shown in FIG. 5B, sensor 500 includes cylindrical core element 502 (which may be solid, hollow or otherwise permeable), such as a mandrel, with a portion of fiber optic cable 402, with cladding 402b exposed (in this example), wrapped around core element 502 over a predetermined length 506. It is also possible to fabricate sensor 500 by wrapping core element 502 where core 402c of fiber optic cable 402 is exposed. The diameter of core element 502 is such that fiber core 402c is formed with less than a critical radius r, at which point excess radiation may be lost through fiber core 402c as it circumscribes core element 502, or fiber integrity is compromised. The critical radius r is dependent on the frequency of the radiation passing through fiber optic cable 402 and/or the composition of the fiber. In a preferred embodiment of the present invention, the radius of core element 502 is between about 1 cm and 10 cm, and most preferably at least about 1 cm. As illustrated, radiation from fiber 402 is provided at input 504 and extracted at output 508. Cylindrical core element 502 may have a spiral groove on its surface in which fiber 402 is placed as well as a means to secure fiber 402 to cylindrical core element 502. Such securing means may take may forms, such as a screw tapped into cylindrical core element 502, an adhesive, such as epoxy or silicon rubber, etc. The invention may be practiced where sensors 500 are integral with fiber 402 or may be coupled to fiber 402 utilizing commercially available fiber-optic connectors.

Figure 6A:
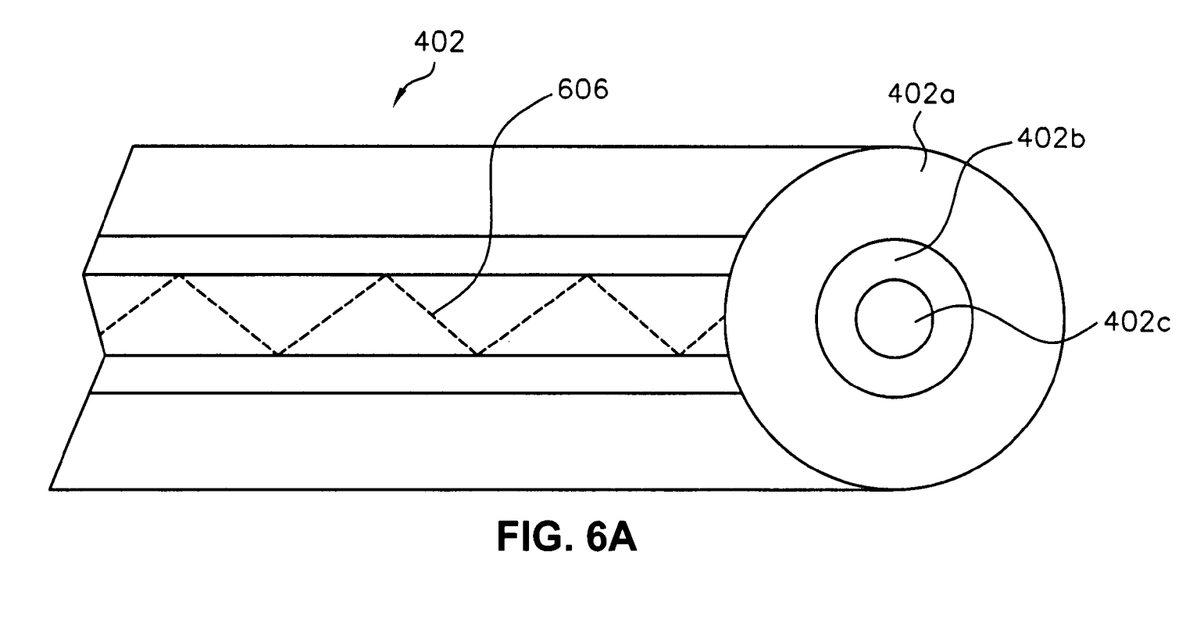
FIG. 6A is a cross sectional view of fiber optic cable illustrating propagation of radiation within the cable.

FIG. 6A illustrates how radiation propagates through a typical fiber optic cable. As shown in FIG. 6A, radiation 606 exhibits total internal reflection (TIR) at the boundary between inner core 402c and cladding 402b. There is some negligible loss (not shown) by which radiation is not reflected, but is absorbed into cladding 402b. Although FIG. 6A is described as a fiber optic cable, FIG. 6A and the exemplary embodiments of the present inventions are equally applicable to a hollow fiber, such as a hollow waveguide, in which cladding 402b surrounds a hollow core.

Figure 6B:
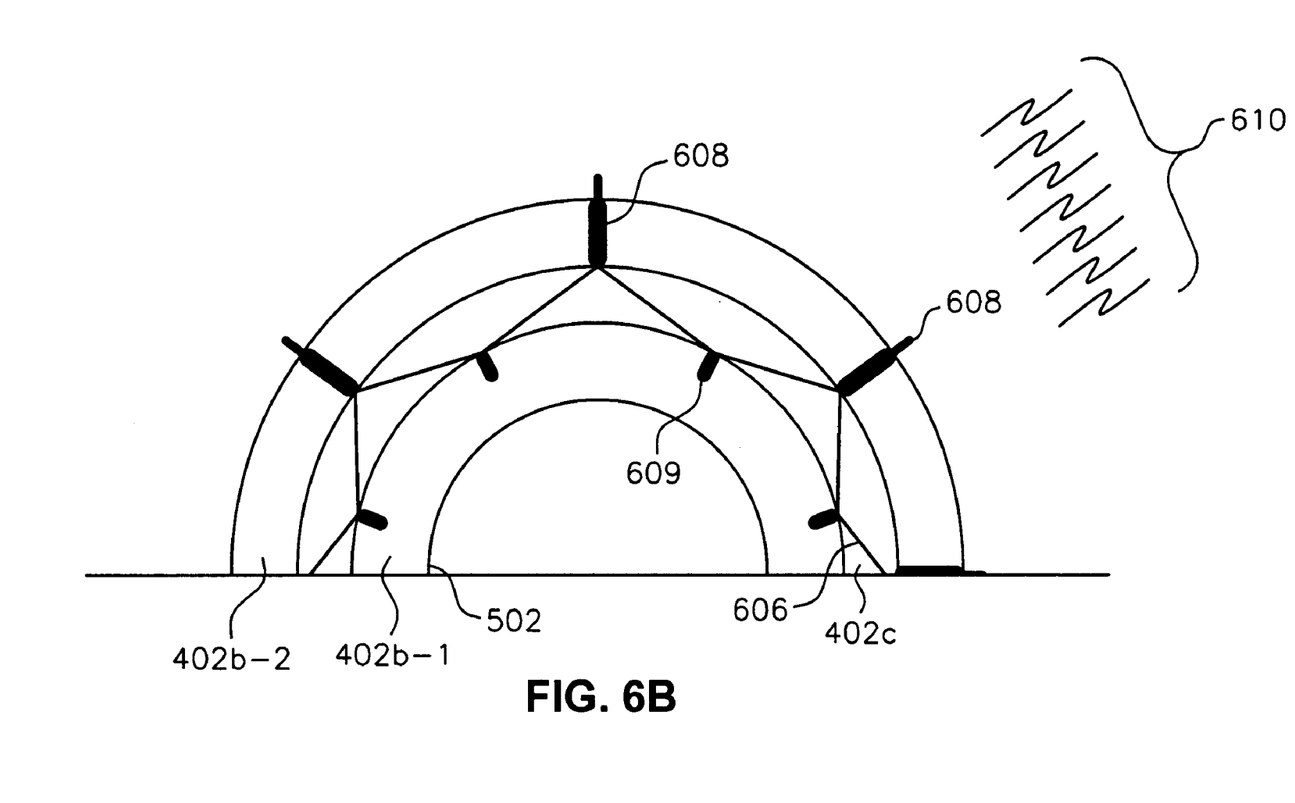
FIG. 6B is a cross section of a fiber optic sensor illustrating the evanescent field according to an exemplary embodiment of the present invention

FIG. 6B is a cross sectional view of one exemplary embodiment of sensor 500 which illustrates the effect of wrapping fiber optic cable 402 around core element 502. As shown in FIG. 6B, only jacket 402a is removed from fiber optic cable 402. Radiation 606 travels within core 402c and exhibits total internal reflection at the boundary between inner core 402c and the portion of cladding 402b-1 adjacent core element 502 with a negligible loss 609. On the other hand, in the presence of trace species or analyte 610, evanescent field 608 passes through the interface between inner core 402c and the exposed portion of cladding 402b-2. This essentially attenuates radiation 606 based on the amount of trace species 610 present and is called attenuated total internal reflection (ATR). It should be noted that if there is no a trace species present having an absorption band compatible with the wavelength of the radiation, radiation 606 is not attenuated (other than by inherent loss in the fiber).

Figure 6C:
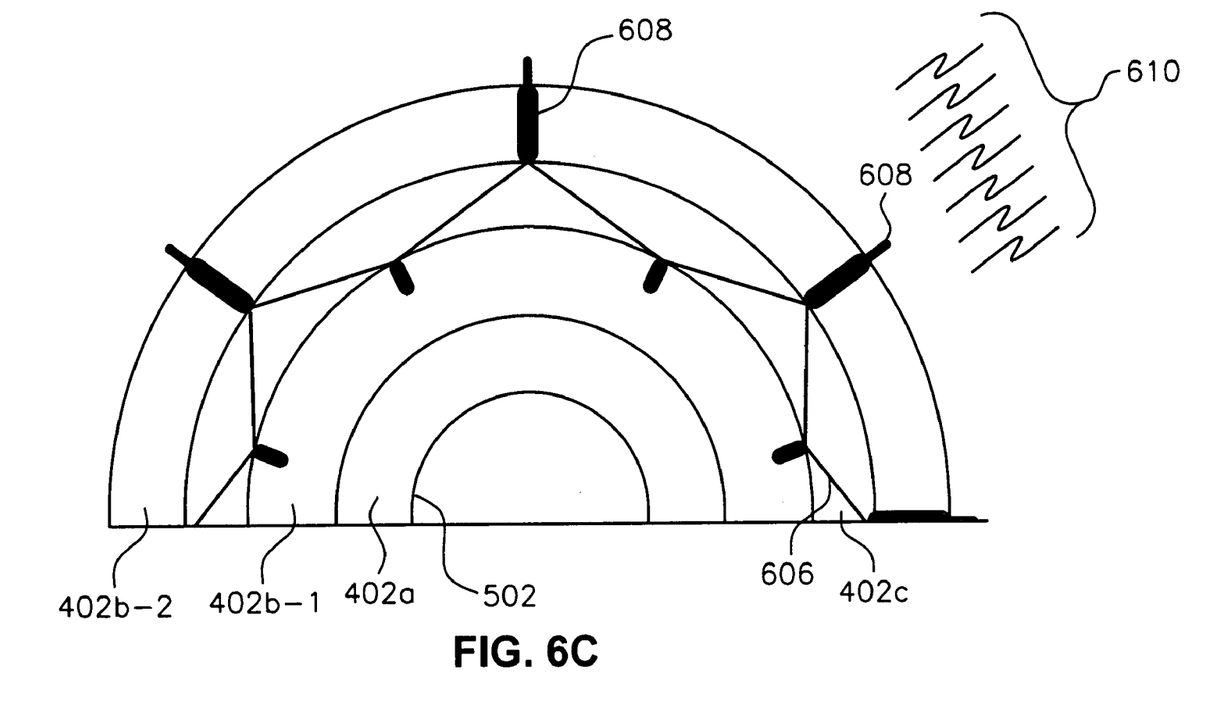
FIG. 6C is a cross section of a fiber optic sensor illustrating the evanescent field according to another exemplary embodiment of the present invention.
Figure 6D:
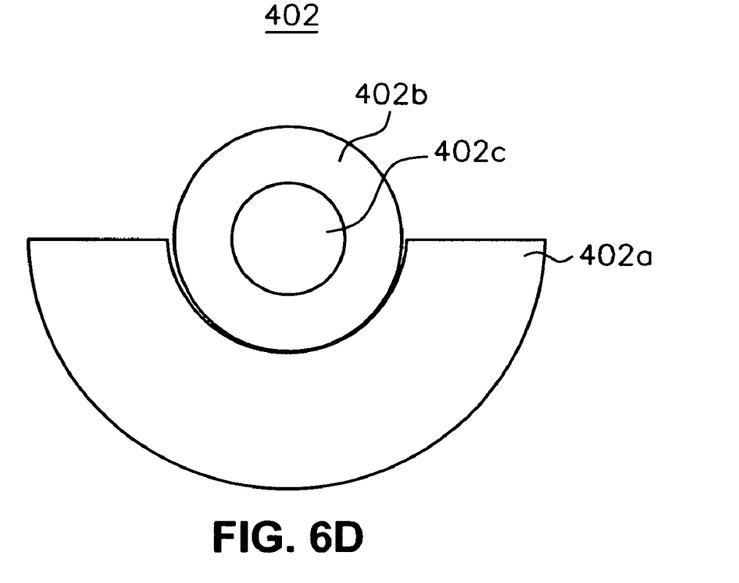
FIG. 6D is a cross-section of a fiber optic sensor according to another exemplary embodiment of the present invention.

FIG. 6C is a cross sectional view of another exemplary embodiment of sensor 500 which illustrates the effect of wrapping fiber optic cable 402 around core element 502 with a portion of jacket 402a remaining intact. As shown in FIG. 6D, only an upper portion of jacket 402a is removed from fiber optic cable 402. Similar to the first exemplary embodiment of sensor 500, radiation 606 travels within core 402c and exhibits total internal reflection at the boundary between inner core 402c and the portion of cladding 402b-1 adjacent core element 502 with negligible loss 609. On the other hand, in the presence of trace species or analyte 610 evanescent field 608 passes through the interface between inner core 402c and the exposed portion of cladding 402b-2.

It is contemplated that the removal of jacket 402a (in either example of sensor 500) may be accomplished by mechanical means, such as a conventional fiber optic stripping tool, or by immersing the portion of the fiber cable in a solvent that will attack and dissolve jacket 402a without effecting cladding 402b and inner core 402c. In the case of partial removal of jacket 402a, the solvent approach may be modified by selectively applying the solvent to the portion of the jacket intended for removal.

To enhance the attraction of analyte molecules of the trace species in a liquid sample, a jacket-less portion of the passive fiber optic ring may be coated with a material to selectively increase a concentration of the trace species at the coated portion of the fiber optic ring. An example of one such coating material is polyethylene. Additionally, antigen specific binders may be used to coat the fiber to attract a desired biological analyte with high specificity.

Referring again to FIG. 4, the radiation that remains after passing through sensors 500 continues through fiber loop 402. A portion of that remaining radiation is coupled out of fiber optic loop 402 by evanescent output coupler 416. Evanescent output coupler 416 is coupled to processor 420 through detector 418 and signal line 422. Processor 420 may be a PC, for example, having a means for converting the analog output of detector 418 into a digital signal for processing. Processor 420 also controls coherent source 404 through control line 424. Once the signals are received from detector 418 by processor 420, the processor may determine the amount and type of trace species present based the decay rate of the radiation received.

Optionally, wavelength selector 430 may be placed between evanescent output coupler 416 and detector 418. Wavelength selector 430 acts as a filter to prevent radiation that is not within a predetermined range from being input into detector 418.

Detector 414 is coupled to the output of input coupler 412. The output of detector 414 is provided to processor 420 via signal line 422 for use in determining when resonant fiber optic ring 402 has received sufficient radiation by which to perform trace species analysis.

In the case of detection of trace species or analytes in liquids, the index of refraction of the liquid must be lower than the index of refraction of the fiber optic cable. For example, given a fiber optic cable having an index of refraction of n=1.46, the invention may be used to detect trace species dissolved in water (n=1.33) and many organic solvents, including methanol (n=1.326), n-hexane (n=1.372), dichloromethane (n=1.4242), acetone (n=1.3588), diethylether (n=1.3526), and tetrahydrofuran (n=1.404), for example. An extensive list of chemicals and their respective index of refraction may be found in CRC *Handbook of Chemistry and Physics, 52$^{nd}$ edition,* Weast, Rober C., ed. The Chemical Rubber Company: Cleveland Ohio, 1971, p. E-201, incorporated herein by reference. There are other types of optical fiber available with different indexes of refraction, and the present invention can be tailored to a given liquid matrix assuming the optical fiber has both a higher index of refraction than the liquid and effectively transmits light in the region of an absorption band by the target analyte.

There are many different types of optical fiber currently available. One example is Corning's SMF-28e fused silica fiber which has a standard use in telecommunications applications. Specialty fibers exist that transmit light at a multitude of different wavelengths, such as a 488 nm/514 nm single mode fiber, manufactured by 3M of Austin, Tex. (part no. FS-VS-2614), 630 nm visible wavelength single-mode fiber manufactured by 3M of Austin, Tex. (part no. FS-SN-3224), 820 nm standard single-mode fiber manufactured by 3M of Austin, Tex. (part no. FS-SN-4224), and 0.28-NA fluoride glass fiber with 4-micron transmission, manufactured by KDD Fiberlabs of Japan (part no. GF-F-160). Further, and as mentioned above, fiber optic cable 402 may be a hollow fiber.

It is contemplated that fiber 402 may be a mid-infrared transmitting fiber to allow for access to spectral regions having much higher analyte absorption strengths, thereby increasing the sensitivity of the apparatus 400. Fibers that transmit radiation in this region are typically made from fluoride glasses.

Figure 7:
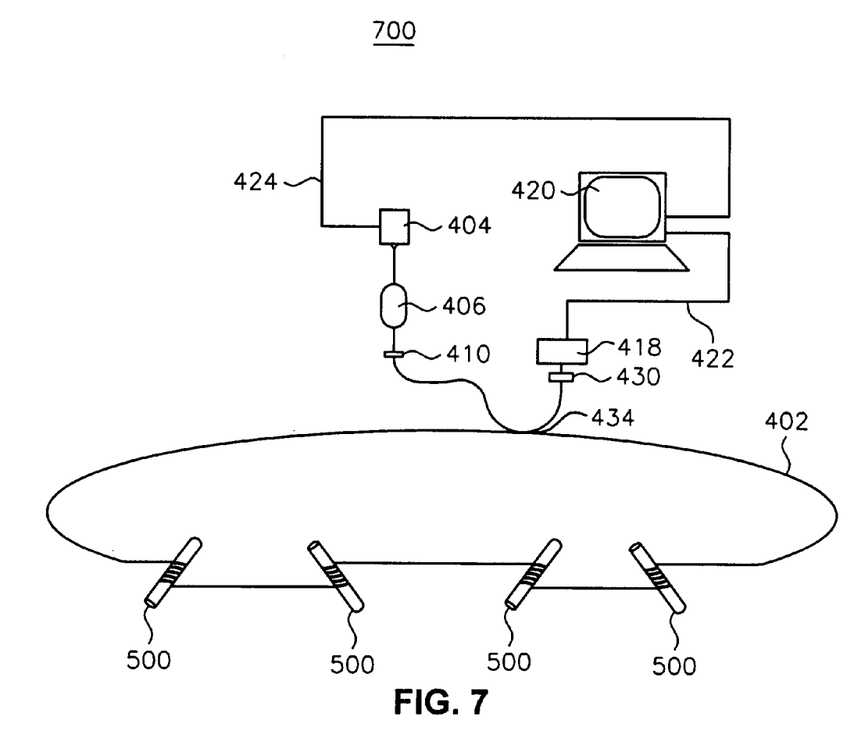
FIG. 7 is an illustration of a second exemplary embodiment of the present invention.

FIG. 7 illustrates a second exemplary embodiment of the present invention through which trace species, or analytes, in gases and liquids may be detected. In describing FIG. 7, elements performing similar functions to those described with respect to the first exemplary embodiment will use identical reference numerals. In FIG. 7, apparatus 700 uses a similar resonant fiber optic ring 408 including fiber optic cable 402 and sensors 500. Radiation from coherent source 404 is provided to resonant fiber optic ring 408 through optional optical isolator 406, coupler 410, and evanescent input/output coupler 434. Evanescent input/output coupler 434 may provide a fixed percentage of radiation from coherent source 404 into resonant fiber optic ring 408, or may be adjustable based on losses present throughout resonant fiber optic ring 404. In the exemplary embodiment evanescent input/output coupler 434 is essentially a reconfiguration of evanescent input coupler 412 discussed above with respect to the first exemplary embodiment. It a preferred embodiment, evanescent input/output coupler 434 couples less that 1% of the radiation from laser 404 into fiber 402.

Detection of trace species is similar to that described in the first exemplary embodiment and is therefore not be repeated here.

The radiation that remains after passing through sensors 500 continues through fiber loop 402. A portion of that remaining radiation is coupled out of fiber optic loop 402 by evanescent input/output coupler 434. Evanescent input/output coupler 434 is coupled to processor 420 through detector 418 and signal line 422. As in the first exemplary embodiment, processor 420 also controls coherent source 404 through control line 424. Once the signals are received from detector 418 by processor 420, the processor may determine the amount and type of trace species present based the decay rate of the radiation received.

Optionally, wavelength selector 430 may be placed between evanescent input/output coupler 434 and detector 418. Wavelength selector 430 acts as a filter to prevent radiation that is not within a predetermined range from being input into detector 418. Wavelength selector 430 may also be controlled by processor 420 to prevent radiation from coherent source 404 "blinding" detector 418 during the time period after the radiation from coherent source 404 was coupled into fiber 402.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. An apparatus for detection and measurement of trace species in at least one of a sample gas and/or a sample liquid comprising:
    a closed passive fiber optic ring having a portion thereof exposed to the sample gas and/or sample liquid;
    a coherent source of radiation;
    coupling means for i) introducing a portion of the radiation emitted by the coherent source to the closed passive fiber optic ring and ii) receiving a portion of the radiation resonant in the closed passive fiber optic ring;
    a detector for detecting a level of the radiation received by the coupling means and generating a signal responsive thereto; and
    a processor coupled to the detector for determining a level of the trace species in the gas sample and/or liquid sample based on the signal generated by the detector.

2. The apparatus according to claim 1, wherein the level of the trace species is determined based on a rate of decay of the signal generated by the detector.

3. The apparatus according to claim 1, wherein the coupling means is a single optical coupler.

4. The apparatus according to claim 3, further comprising a filter placed in an optical path between the coupling means and the detector to selectively pass the received portion of radiation from the passive fiber optic loop to the detector.

5. The apparatus according to claim 4, wherein the filter passes radiation to the detector based on a wavelength of the radiation.

6. The apparatus according to claim 1, wherein the coupling means includes i) a first coupler for introducing the portion of the radiation emitted by the coherent source to a first section of the fiber optic ring and ii) a second coupler for receiving the portion of the radiation in the passive fiber optic ring at a second section thereof.

7. The apparatus according to claim 1, wherein the exposed portion is a cladding of the fiber.

8. The apparatus according to claim 1, wherein the exposed portion is an inner core of the fiber.

9. The apparatus according to claim 1, wherein coherent source of radiation is an optical parametric generator.

10. The apparatus according to claim 1, wherein coherent source of radiation is an optical parametric amplifier.

11. The apparatus according to claim 1, wherein coherent source of radiation is a laser.

12. The apparatus according to claim 1, wherein the coherent source of radiation is a pulsed laser.

13. The apparatus according to claim 1, wherein the coherent source of radiation is a continuous wave laser.

14. The apparatus according to claims 11, 12 or 13, wherein the laser is an optical fiber laser.

15. The apparatus according to claim 13, wherein the continuous wave laser is a tunable diode laser having a narrow band.

16. The apparatus according to claim 15, further comprising an isolator coupled between the laser and the coupling means and in line with the radiation emitted from the laser, the isolator minimizing noise in the laser.

17. The apparatus according to claim 1, wherein an evanescent field of the radiation traveling within the fiber is exposed to the sample gas or sample liquid.

18. The apparatus according to claim 17, wherein the absorption of the radiation from the fiber increases a rate of decay of the radiation received by the coupling means.

19. The apparatus according to claim 1, wherein the passive resonant fiber is formed from one of fused silica, sapphire and fluoride based glass.

20. The apparatus according to claim 1, wherein the passive resonant fiber is formed from a hollow fiber.

21. The apparatus according to claims 19 or 20, wherein the passive resonant fiber is a single mode fiber.

22. The apparatus according to claims 19 or 20, wherein the passive resonant fiber is a multi-mode fiber.

23. The apparatus according to claim 1, further comprising at least one cylindrical body having a predetermined diameter and wrapped with the exposed portion of the optical fiber, wherein exposure of the evanescent field to the trace species is enhanced by increasing a penetration depth of the evanescent field.

24. The apparatus according to claim 1, further comprising a plurality of cylindrical bodies having respective predetermined diameters and wrapped with respective sections of the exposed portion of the resonant fiber.

25. The apparatus according to claims 23 or 24, wherein the tubular structure is a mandrel.

26. The apparatus according to claim 25, wherein the mandrel has a cross sectional radius of at least about 1 cm.

27. The apparatus according to claim 25, wherein the mandrel has a cross sectional radius of between about 1 cm and 10 cm.

28. The apparatus according to claim 1, wherein the trace species is at least one of water, acetylene and ammonia.

29. The apparatus according to claim 28, wherein the coherent source is a single mode laser tunable in the wavelength region of about 1390 nm and about 1513 nm.

30. The apparatus according to claim 1, wherein the passive fiber optic ring resonates at a wavelength between a visible to a mid-infrared region of an electro-magnetic spectrum.

31. The apparatus according to claim 1, wherein at least a portion of the passive fiber optic ring is disposed within the liquid sample for determining a presence of the trace species in the liquid sample.

32. The apparatus according to claim 1, wherein at least a portion of the passive fiber optic ring is coated with a material to selectively increase a concentration of the trace species at the coated portion of the fiber optic ring.

33. The apparatus according to claim 32, wherein the material attracts analyte molecules of the trace species.

34. The apparatus according to claim 33, wherein the material is polyethylene.

35. The apparatus according to claim 32, wherein at least the coated portion of the passive fiber optic ring is disposed within the liquid sample for determining a presence of the trace species in the liquid sample.

36. The apparatus according to claim 1, further comprising an input detector for determining when energy from the laser is provided to the fiber optic ring.

37. The apparatus according to claim 36, further comprising control means to deactivate the laser based on the receiving means receiving radiation from the fiber optic ring after the input detector determines that the laser provided energy to the fiber optic ring.

38. The apparatus according to claim 37, wherein the control means and the input detector are coupled to the processing means.

39. The apparatus according to claim 1, wherein an index of refraction of the fiber is greater than an index of refraction of the sample liquid.

40. The apparatus according to claim 1, wherein an index of refraction of the fiber is based on an index of refraction of the sample gas and an absorption band of the trace species.

41. The apparatus according to claim 1, wherein the portion of the radiation coupled into the fiber optic ring is less than about 1% of the radiation provided to the coupling means.

42. The apparatus according to claim 1, wherein the portion of the radiation coupled into the fiber optic ring is variable.

43. The apparatus according to claim 1, wherein the portion of the radiation coupled into the fiber optic ring is varied based on a loss within the passive fiber optic loop.

44. The apparatus according to claim 43, wherein the loss within the passive fiber optic loop is based on at least connector losses and fiber losses.

45. The apparatus according to claim 1, wherein the fiber optic ring is at least about 1 meter long.

46. The apparatus according to claim 1, wherein the fiber optic ring is at least about 10 meters long.

47. The apparatus according to claim 1, wherein the fiber optic ring is at least about 1 Km long.

48. An apparatus for detection and measurement of trace species in at least one of a sample gas and/or a sample liquid comprising:
    a closed passive resonant fiber optic ring having a portion exposed to the sample gas or sample liquid;
    a coherent source emitting radiation;
    a first optical coupler to provide at least a portion of the radiation emitted by the coherent source to a first section of the closed passive resonant fiber ring;
    at least one cylindrical body coupled to a portion of the exposed fiber optic ring to form the portion of the exposed fiber optic ring with a predetermined radius, at least a portion of the sample liquid and/or sample gas contacting the formed portion of the closed fiber optic ring;
    a second optical coupler for receiving a portion of the radiation in the closed passive resonant fiber ring from a second section of the closed resonant fiber ring; and
    a processor coupled to the second optical coupler for determining a level of the trace species in the gas an/or liquid sample based on a rate of decay of the radiation received by the second optical coupler.

49. The apparatus according to claim 48, further comprising a first optical detector coupled between the second optical coupler and the processor for generating a signal responsive to the radiation received by the second optical coupler.

50. The apparatus according to claim 48, further comprising a second optical detector coupled between the first optical coupler and the processor for determining when energy from the laser is provided to the passive fiber optic ring.

51. The apparatus according to claim 50, wherein the second optical detector generates a trigger signal to the processor responsive to receiving radiation from the coherent source.

52. The apparatus according to claim 48, wherein the first and second optical couplers are a unitary coupler.

53. A method for detecting and measuring a trace species in at least one of a sample gas and/or a sample liquid, the method comprising:
    exposing a portion of an optic fiber of a closed passive fiber optic ring to the sample gas and/or sample liquid;
    emitting radiation from a coherent source;
    coupling at least a portion of the radiation emitted from the coherent source into the closed passive fiber optic ring;
    receiving a portion of the radiation traveling in the closed passive fiber optic ring; and
    determining the level of trace species in the gas and/or liquid sample based on a rate of decay of the radiation within the closed passive fiber optic ring.

54. A method according to claim 53, further comprising:
    forming, with a predetermined radius, at least a portion of the exposed portion of the passive fiber optic ring based on an absorption frequency of the trace species; and
    exposing the formed portion of the fiber to the sample liquid or sample gas.

55. A method according to claim 54, further comprising exposing an evanescent field of the radiation traveling within the fiber to the sample gas or sample liquid.

56. A method according to claim 55, further comprising determining the level of the trace species in the sample gas or sample liquid based on the rate of decay of the radiation in the fiber responsive to an absorption of the radiation by the trace species.

* * * * *